US010258423B2

(12) United States Patent
Roland

(10) Patent No.: US 10,258,423 B2
(45) Date of Patent: Apr. 16, 2019

(54) SURGICAL INSTRUMENT ORGANIZER

(71) Applicant: Lincoln Roland, Tallahassee, FL (US)

(72) Inventor: Lincoln Roland, Tallahassee, FL (US)

( * ) Notice: Subject to any disclaimer, the term of this patent is extended or adjusted under 35 U.S.C. 154(b) by 330 days.

(21) Appl. No.: 15/227,734

(22) Filed: Aug. 3, 2016

(65) Prior Publication Data
US 2017/0035522 A1 Feb. 9, 2017

Related U.S. Application Data

(60) Provisional application No. 62/200,334, filed on Aug. 3, 2015.

(51) Int. Cl.
*A61B 50/22* (2016.01)
*A61B 50/20* (2016.01)
*A61B 90/00* (2016.01)
*A61B 50/30* (2016.01)

(52) U.S. Cl.
CPC .............. *A61B 50/22* (2016.02); *A61B 50/20* (2016.02); *A61B 90/08* (2016.02); *A61B 50/30* (2016.02)

(58) Field of Classification Search
CPC ......... A61B 50/20; A61B 50/22; A61B 50/30; A61B 90/08
See application file for complete search history.

(56) References Cited

U.S. PATENT DOCUMENTS

| | | | |
|---|---|---|---|
| 3,770,119 A | | 11/1973 | Hultberg et al. |
| 4,523,679 A | * | 6/1985 | Paikoff ...................... A61L 2/04 |
| | | | 206/363 |
| 5,441,152 A | | 8/1995 | Estes |
| 5,611,780 A | | 3/1997 | Decarie et al. |
| 6,196,503 B1 | | 3/2001 | Cernosek et al. |
| 8,286,794 B1 | | 10/2012 | Agadzi |
| 8,371,448 B1 | * | 2/2013 | Reaux .................... A61B 50/13 |
| | | | 206/362 |

* cited by examiner

*Primary Examiner* — Brandy S Lee
(74) *Attorney, Agent, or Firm* — Global Intellectual Property Agency, LLC; Daniel Boudwin

(57) ABSTRACT

A surgical instrument organizer. The surgical instrument organizer includes an upper assembly affixed to a lower assembly. The upper assembly includes a recessed area for supporting surgical instruments, one or more catheters extending therefrom, and one or more clips for supporting tubes, cables, and the like. In one embodiment, the catheters are operably connected to a valve that controls passage therethrough. The lower assembly includes one or more chambers accessible via one or more ports. In one embodiment, a channel and tube causes the upper assembly to be in fluid communication with the chambers of the lower assembly, wherein cleaning solution may be added or removed from the chambers as desired. Each port of the lower assembly is configured to receive wires for cleaning the chambers of blood or other fluids.

13 Claims, 3 Drawing Sheets

SURGICAL INSTRUMENT ORGANIZER

CROSS REFERENCE TO RELATED APPLICATION

This application claims the benefit of U.S. Provisional Application No. 62/200,334 filed on Aug. 3, 2015. The above identified patent application is herein incorporated by reference in its entirety to provide continuity of disclosure.

BACKGROUND OF THE INVENTION

The present invention elates to a surgical instrument organizer. More specifically, the present invention relates to a surgical instrument organizer that utilizes an upper and lower assembly for storing surgical instruments and medications.

Modern day surgery involves the use of a wide variety of different surgical instruments, including catheters, scalpels, and other kinds of tools. These instruments are typically of various types and designs to effect a variety of surgical in a medical or hospital operating room environment. It is desirable to have these surgical instruments organized or collected in a particular sequence and layout for use in specific surgical procedures.

As a result of the unorganized manner by which items are gathered for surgery, the surgical operation itself becomes more difficult. For example, endovascular procedures utilizes catheters, tubes having a guidewire running therethrough that are inserted into a patient. These catheters needs to be sterile to prevent infection, and often need to be cleaned intermittently to prevent complications during surgery. However, additional catheters and equipment for cleaning or otherwise assisting with the surgical procedures are not typically positioned in a centralized location that is easily accessible to the surgical team.

If the surgical instruments, medications, and other equipment are not organized prior to surgery, the surgeon may have to sort through the resulting clutter to find the instrument he or she is looking for. The clutter typically increases throughout the operation as the surgeon uses different tools and instruments and places them back on the table. Any increased operating time resulting from the lack of instrument management increases the overall cost of the surgery and can compromise the quality of the operation. Additionally, the lack of instrument management increases the potential of accidental injury from exposed scalpel blades and the like.

A variety of devices exist for storing surgical instruments. However, these devices have several deficiencies. For example, one device is a medical organizer for organizing cable-tubing via attachment mechanisms. These known devices fail to provide a device that utilizes an upper and lower assembly for storing surgical instruments, such as catheters, wires, and medications.

In light of the devices disclosed in the known art, it is submitted that the present invention substantially diverges in design elements from the known art and consequently it is clear that there is a need in the art for an improvement to surgical instrument organizers. In this regard the instant invention substantially fulfills these needs.

SUMMARY OF THE INVENTION

In view of the foregoing disadvantages inherent in are known types of surgical organizer devices now present in the known art, the present invention provides a surgical instrument organizer comprising an upper assembly affixed to a lower assembly. The upper assembly includes a recessed area for supporting surgical instruments, one or more catheters extending therefrom, and one or more clips for supporting tubes, cables, and the like. In one embodiment, the catheters are operably connected to a valve that controls passage therethrough. The valve may be a three way stop cock valve that is also operably connected to a waste tube leading to a waste compartment within the surgical instrument organizer that is configured to store waste material. The lower assembly includes one or more chambers configured to house fluid, wherein the chambers are accessible via one or more ports. In one embodiment, a tube causes the upper assembly to be in fluid communication with the chambers of the lower assembly, wherein cleaning solution may be added or removed from the chambers as desired. Each port of the lower assembly is configured to receive the catheters and wires of the upper assembly and clean them via the solution.

It is therefore an object of the present invention to provide a new and improved surgical instrument organizer that has all of the advantages of the prior art and none of the disadvantages.

It is another object of the present invention to provide a surgical instrument organizer for supporting various medical equipment used in an operating room and providing a centralized device for assisting with the performance of surgical procedures involving catheters and the like.

It is therefore an object of the present invention to provide a surgical instrument organizer that allows surgeons and surgical assistants to organize the operating room quickly while easily having access to surgical instruments necessary for the completion of surgical procedures.

Other objects, features and advantages of the present invention will become apparent from the following detailed description taken in conjunction with the accompanying drawings.

BRIEF DESCRIPTIONS OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
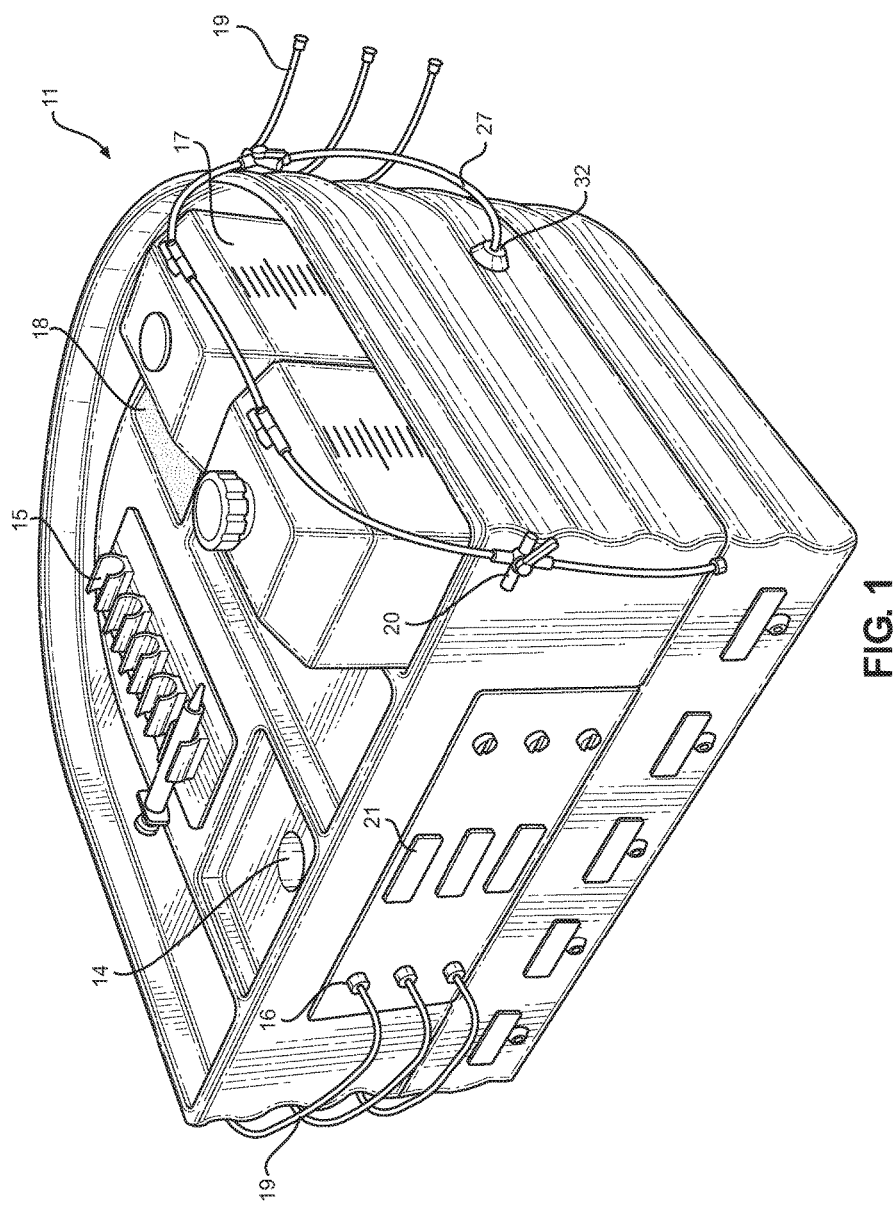
FIG. 1 shows a perspective view of one embodiment of the surgical instrument organizer.

Reference is made herein to the attached drawings. Like reference numerals are used throughout the drawings to depict like or similar elements of the surgical instrument organizer. For the purposes of presenting a brief and clear description of the present invention, the preferred embodiment will be discussed as used for assisting with endovascular surgical procedures. The figures are intended for representative purposes only and should not be considered to be limiting in any respect.

Referring now to FIG. 1 there is shown a perspective view of one embodiment of the surgical instrument organizer. The surgical instrument organizer 11 provides a device for organizing surgical tools and instruments to assist with the performance of surgery on a patient. The surgical instrument organizer 11 comprises an upper assembly 12 removably affixed to a lower assembly 13. The upper assembly 12 includes one or more clips 15 configured to retain syringes, medication and other such articles, a track configured to receive one or more containers 17, and one or more catheters 19 each extending from an opening. The catheters 19 may include catheters, wires, tubes and the like. The upper assembly 12 includes a sponge 18 configured to hold syringes and blades in a safe manner.

In the shown embodiment, surgical instrument organizer 11 has a semicircular shape. The upper and lower assembly 12, 13 are substantially similar in shape and when affixed, are flush with each other. In alternative embodiments, the shape of the upper and lower assemblies 12, 13 may be different from each other. In one embodiment, the one or more clips 15, a channel 14, the recessed area 41, and the sponge 18 are disposed on the upper surface of the upper assembly 12. In alternative embodiments, the position of these elements may vary.

Figure 2:
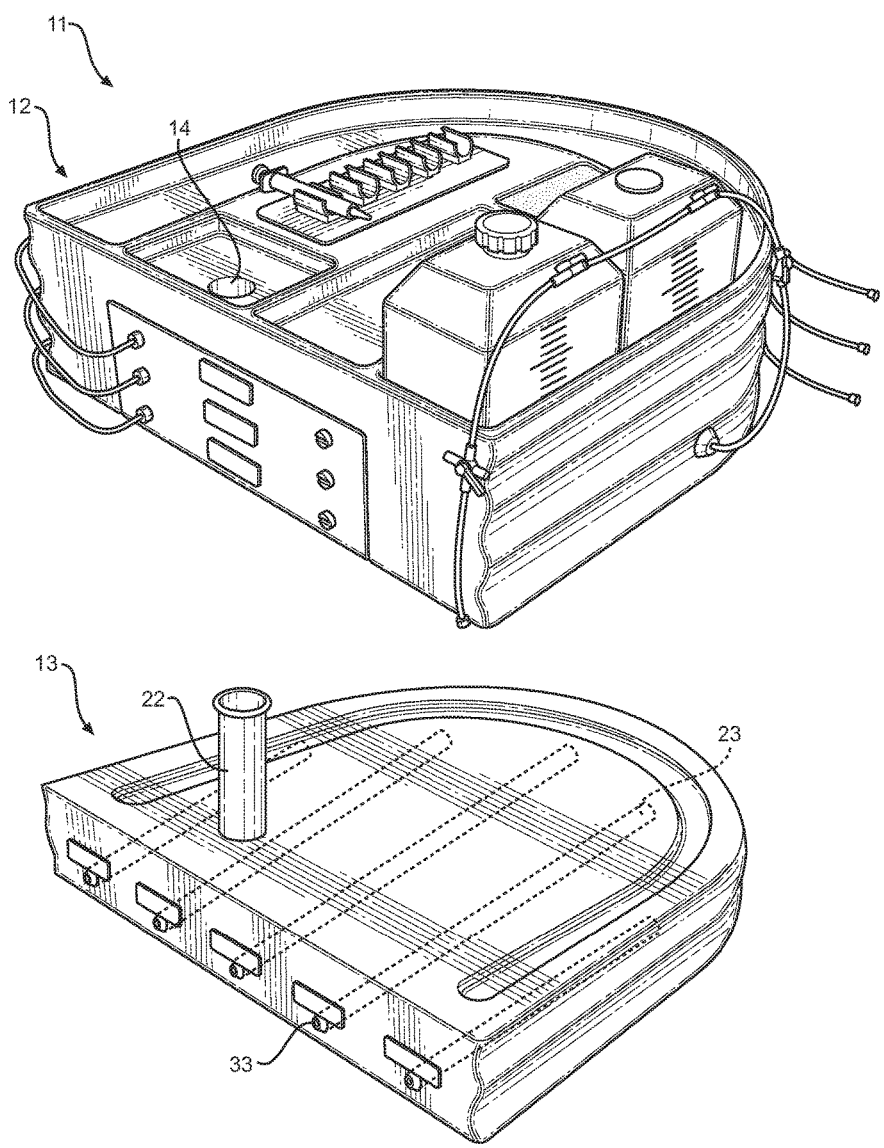
FIG. 2 shows an exploded view of one embodiment of the surgical instrument organizer.

Referring now to FIG. 2, there is shown an exploded view of one embodiment of the surgical instrument organizer. In the shown embodiment, the upper assembly 12 is in fluid communication with the lower assembly 13 via a pipe 22. The pipe 22 extends upward from the lower assembly 13 and is configured to connect to the channel 14 of the upper assembly 12. In this way, the channel 14 and the pipe 22 are configured to fill one or more chambers 23 disposed in the lower assembly 13 with fluid, such as saline or other solution, wherein the chambers 23 are configured to house the fluid. The chambers 23 are accessible via one or more catheter receiving ports 33 that are disposed on the lower assembly 13. The ports 33 and the chambers 23 of the lower assembly 13 are configured to receive the catheters of the upper assembly 12. In one use, a user can insert a wire into one of the chambers 23 through port 33 and move the wire back and forth therein. The fluid of the chamber 23 and the movement assist with removing any dried blood or residue located on the wire.

In the shown embodiment, the chambers 23 are tubular ducts that extend longitudinally along the lower assembly 13. The chamber 23 are disposed parallel relative to one another and are aligned with the ports 33. In alternative embodiments, the one or more chambers 23 may have any shape and orientation. For example, the chambers 23 may be coiled or serpentine shaped. In yet another embodiment, the one or more chambers 23 are in fluid communication with each other forming a single chamber. The ports 33 may include brushes thereon that are adapted to clean the wires as they are inserted through the ports 33.

Figure 3:
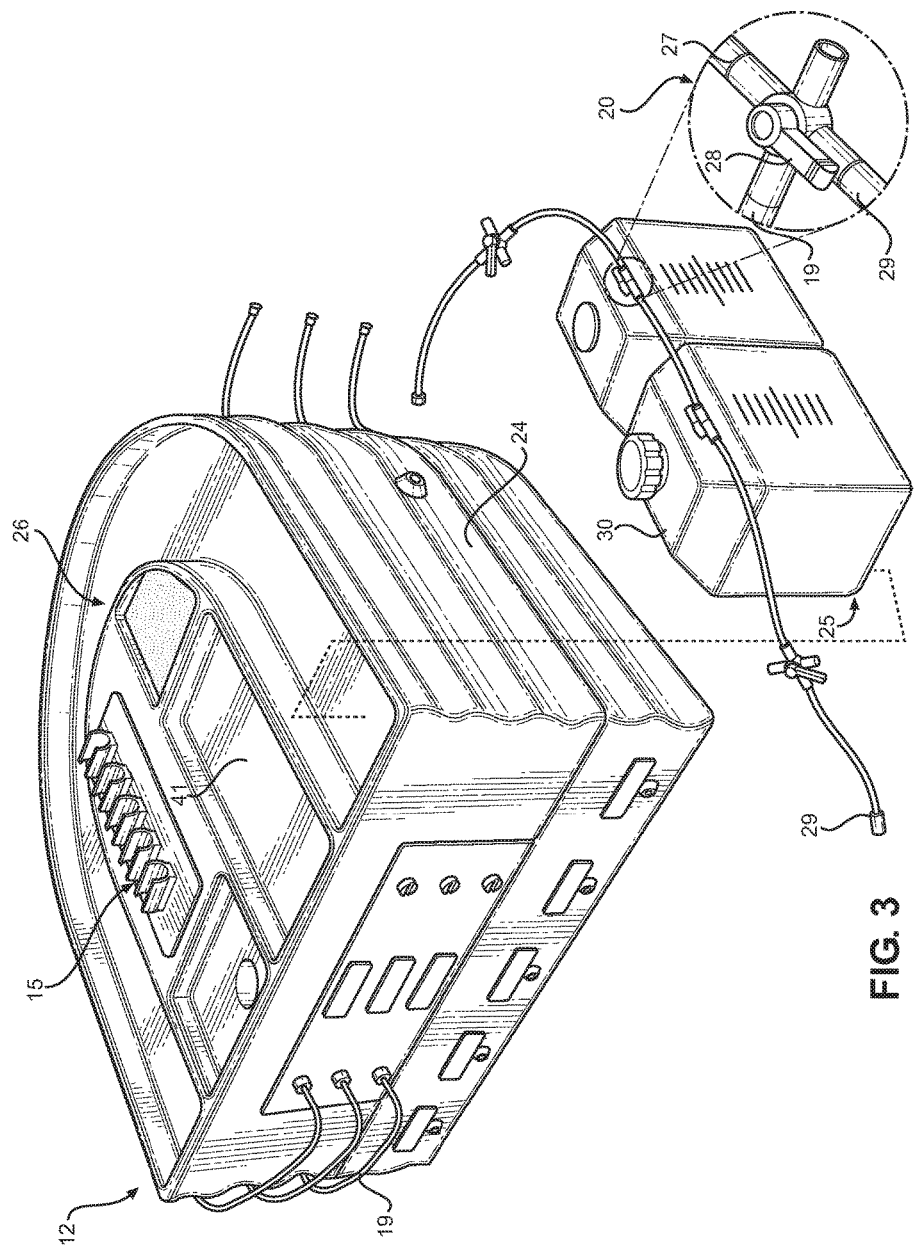
FIG. 3 shows a detailed view of one embodiment of the valve of the surgical instrument organizer.

Referring now to FIG. 3, there is shown a detailed view of one embodiment of the valve of the surgical instrument organizer. In the shown embodiment, the one or more catheters 19 extend from the upper assembly 12. The upper assembly 12 comprises one or more grooves 24 disposed along the perimeter thereof, wherein the one or more grooves 24 are configured to retain the one or more catheters 19 therein. The grooves 24 help organize the catheters 19 during surgical procedures to prevent them from becoming tangled, disorganized, and the like.

A valve 20 is operably connected with one of the catheters 19, wherein the valve 20 is configured to control the passage of fluids therethrough. In one embodiment, the valve 20 is a three-way valve, such as a stop cock valve, that operably connected to a waste tube 27. In the shown embodiment, the three-way valve 20 is operably connected to the catheter 19, the waste tube 27, and a patient line 29. The waste tube 27 is in fluid communication with a waste compartment (not shown) within the surgical instrument organizer 11 wherein the waste compartment is configured to store waste material. The patient line 29 may be a catheter, a wire, a tube, or the like. The three-way valve 20 includes an actuator 28 that is configured to control the passage and flow of fluids through the valve 20. In one embodiment, the actuator 28 causes an obstructive member to alter s position and control the flow of fluids or wires through the valve 20 and the operably connected components: the one of the catheter 19, the waste tube 27, or the patient line 29. In one use, the valve 20 is configured to allow communication only between catheter 19 and patient line 29. In this way, surgical procedures involving catheters 19 having guidewires are not obstructed by the valve 20. Further, the actuator 28 may be actuated to drain waste material from a patient via the patient line 29 to the waste compartment via the waste tube 27.

The upper assembly 12 further includes a recessed area 41 configured to support and contain surgical equipment, such as gauss pads and the like, thereon. In the shown embodiment, the track 26 of the upper assembly 12 is disposed adjacent to the pen meter of the upper assembly 12. The track 26 is dimensioned to receive one or more containers 17, and the containers 17 can be selectively repositioned within the track 26 as desired. In one embodiment, the one or more containers 17 are slidably engaged with the track 26 allowing the containers 17 to slide between opposing ends thereof. In a preferred embodiment, each of the one or more containers 17 includes volume measuring indicia 25 thereon. For example, the volume measuring indicia 25 may include numerical markings in ascending value that corresponds to the contents of the containers 17.

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A surgical instrument organizer comprising:
   an upper assembly removably affixed to a lower assembly;
   the upper assembly including:
      one or more clips configured to retain cylindrical objects;
      a track configured to receive one or more containers;
      one or more catheters, each of the one or more catheters extending from a port;

the upper assembly in fluid communication with the lower assembly via a pipe extending through a channel disposed on the upper assembly, the lower assembly including one or more chambers, wherein the pipe is configured to fill the one or more chambers with fluid;

each of the one or more chambers configured to receive one of the one or more catheters.

2. The surgical instrument organizer of claim 1, wherein the upper assembly further comprises a sponge configured to hold blades and syringes.

3. The surgical instrument organizer of claim 1, wherein the upper assembly further comprises a recessed area configured to containing gauss pads.

4. The surgical instrument organizer of claim 1, wherein the upper assembly comprises a semicircular shape.

5. The surgical instrument organizer of claim 1, wherein: the track is disposed adjacent to the perimeter of the upper assembly.

6. The surgical instrument organizer of claim 5, wherein: the one or more containers are slidably engageable with the track.

7. The surgical instrument organizer of claim 6, wherein: the one or more containers comprise volume measuring indicia thereon.

8. The surgical instrument organizer of claim 1, wherein: the upper assembly comprises one or more grooves disposed along a perimeter thereof, the one or more grooves configured to retain the one or more catheters therein.

9. The surgical instrument organizer of claim 1, further comprising:

a valve operably connected with the one or more catheters, wherein the valve is configured to control the flow of fluids therethrough.

10. The surgical instrument organizer of claim 9, further comprising:

a waste tube operably connected with the valve, wherein the valve is a three-way valve including an actuator, the actuator configured to control the flow of fluids therethrough.

11. A surgical instrument organizer comprising:

an upper assembly removably affixed to a lower assembly;

the upper assembly including:

one or more clips configured to retain cylindrical objects disposed on a top surface of the upper assembly;

a track configured to receive one or more containers disposed on the top surface of the upper assembly;

one or more catheters, each of the one or more catheters extending from a port disposed on a side surface of the upper assembly;

the upper assembly in fluid communication with the lower assembly via a pipe extending through a channel disposed on the upper assembly, the lower assembly including one or more chambers, wherein the pipe is configured to fill the one or more chambers with fluid;

each of the one or more chambers configured to receive one of the one or more catheters.

12. The surgical instrument organizer of claim 11, wherein a sponge is disposed in a cavity defined by the top surface of the upper assembly.

13. The surgical instrument organizer of claim 11, wherein the upper assembly further comprises a recessed area configured to containing gauss pads.

* * * * *